US009815879B2

(12) United States Patent
Dietrich et al.

(10) Patent No.: US 9,815,879 B2
(45) Date of Patent: Nov. 14, 2017

(54) METHOD FOR THE PURIFICATION OF G-CSF

(75) Inventors: Arndt Dietrich, Reichenbach (DE); Bernhard Janowski, Halle (DE); Jörg Schäffner, Salzmünde (DE); Ulrich Kurt Blaschke, Wiesbaden (DE)

(73) Assignee: Sandoz AG (CH)

( * ) Notice: Subject to any disclaimer, the term of this patent is extended or adjusted under 35 U.S.C. 154(b) by 667 days.

(21) Appl. No.: 11/995,679

(22) PCT Filed: Jul. 14, 2006

(86) PCT No.: PCT/EP2006/064263
§ 371 (c)(1),
(2), (4) Date: Jun. 27, 2008

(87) PCT Pub. No.: WO2007/009950
PCT Pub. Date: Jan. 25, 2007

(65) Prior Publication Data
US 2008/0260684 A1    Oct. 23, 2008

(30) Foreign Application Priority Data

Jul. 15, 2005  (DE) .................... 10 2005 033 250

(51) Int. Cl.
| C07K 14/535 | (2006.01) |
| C07K 1/16 | (2006.01) |
| C07K 1/18 | (2006.01) |
| C07K 1/20 | (2006.01) |
| G01N 30/02 | (2006.01) |

(52) U.S. Cl.
CPC .................... *C07K 14/535* (2013.01)

(58) Field of Classification Search
USPC ........................................................ 210/198.2
See application file for complete search history.

(56) References Cited

U.S. PATENT DOCUMENTS

| 4,658,018 | A | * | 4/1987 | Urdal et al. ................ 530/351 |
| 5,055,555 | A |  | 10/1991 | Sassenfeld |
| 5,331,095 | A |  | 7/1994 | Shadle et al. |
| 2002/0004483 | A1 |  | 1/2002 | Nissen |
| 2002/0142964 | A1 | * | 10/2002 | Nissen et al. ................ 514/12 |
| 2005/0159589 | A1 | * | 7/2005 | Gaberc Porekar et al. .. 530/351 |
| 2008/0260684 | A1 |  | 10/2008 | Dietrich et al. |

FOREIGN PATENT DOCUMENTS

| CN | 1663962 | | 9/2005 |
| DE | 10 2004 041 639 A1 | | 8/2004 |
| EP | 0719860 | | 7/1996 |
| EP | 0335423 | | 3/2003 |
| EP | 1869078 | | 9/2006 |
| EP | 1630173 | | 11/2009 |
| IN | WO 2004/001056 | * | 12/2003 |
| KR | 0160934 | | 4/1998 |
| KR | 100212071 | | 5/1999 |
| WO | WO 87/01132 | | 2/1987 |
| WO | WO 01/04154 A1 | | 1/2001 |
| WO | WO 01/04329 | | 1/2001 |
| WO | WO 02/36626 | | 5/2002 |
| WO | WO 03/102132 | | 4/2003 |
| WO | WO 03/051922 A1 | | 6/2003 |
| WO | WO 2005/049062 A1 | | 6/2005 |
| WO | WO 2006/097944 | | 9/2006 |

OTHER PUBLICATIONS

Amersham Pharmacia Biotech, "Protein Purification Handboo", published in 2001, pp. 1-98.*
Ishizaka, et al., "Mode of action of human urinary colony-stimulating factor," Experimental Hematology, vol. 14, p. 1, (1986). Abstract Only.
Nicola, et al., "Purification of a factor inducing differentiation in murine myelo monocytic leukemia cells identification as granulocyte colony stimulating factor," Journal of Biological Chemistry, vol. 258, p. 9017, (1983). Abstract Only.
Nomura, et al., "Purification and characterization of human granulocyte colony-stimulating factor (G-CSF)," EMBO Journal, vol. 5, No. 5, pp. 871-876, (May 1, 1986).
Römpp Lexikon Umwelt, Stuttgart 1993, pp. 259-260.
International Search Report in six (6) pages for International Application No. PCT/EP2006/064263, filed Jul. 14, 2006.
Amersham Pharmacia Biotech, "Protein Purification Handbook", published in 1999, Chapters 1-3.
Bae, et al., "Improved process for production of recombinant yeast-derived monomeric human G-CSF" *Appl. Microbiol. Biotechnol.* (1999) 52: 338-344.
Devlin, et al., "Alteration of amino-terminal codons of human granulocyte-colony-stimulating factor increases expression levels and allows efficient processing by methionine aminopeptidase in *Escherichia coli,*" Gene (1988) 65: 13-22.
Dietrich, et al., "Industrial Protein Folding" *BIOforum Europe* (2003): 34-36.
Doonan, Shawn and Paul Cutler, "General Strategies" from: *Methods in Molecular Biology*, vol. 244: *Protein Purification Protocols: Second Edition*, Edited by P. Cutler, Humana Press Inc., (2003) Totowa, NJ.
Garg, et al., "Purification and Production of Therapeutic Grade Proteins" from: *Purification and Production of Therapeutic Grade Proteins*, Edited by McGregor, Bioprocess Technology, (1991) New York, NY, 4: 29-54.

(Continued)

*Primary Examiner* — Vanessa L Ford
*Assistant Examiner* — Jegatheesan Seharaseyon
(74) *Attorney, Agent, or Firm* — Luedeka Neely Group, P.C.

(57) ABSTRACT

The present invention relates to a method for obtaining recombinant granulocyte-colony stimulating factor (G-CSF), comprising at least one cation exchange chromatography and at least one hydrophobic interaction chromatography, wherein said two chromatographic steps are immediately consecutive in optional order. In particular, the present invention relates to a method for purifying G-CSF from a mixture of G-CSF and other proteins, comprising two cation exchange chromatography steps which are conducted before and after a hydrophobic interaction chromatography, respectively.

15 Claims, No Drawings

(56) References Cited

OTHER PUBLICATIONS

Herman, et al., "Characterization, Formulation, and Stability of Neupogen® (Filgrastim), a Recombinant Human Granulocyte-Colony Stimulating Factor" from: *Formulation, Characterization, and Stability of Protein Drugs*, Edited by Rodney Pearlman and Y. John Wang, (1996) Plenum Press, New York, NY: 303-328.
Jagschies, Gunter, *Process-Scale Chromatography* (2002) Weickmann & Weickmann, Munich, Germany.
Millipore, *Protein Concentration and Diafiltration by Tangential Flow Filtration* (2003).
Rotondaro, et al., "Purification and Characterization of Two Recombinant Human Granulocyte Colony-Stimulating Factor Glycoforms" *Molecular Biotechnology* (1999) 11: 117-128.
Tsuchiya, et al., "Characterization of recombinant human granulocyte-colony-stimulating factor produced in mouse cells" *EMBO J.* (1987) 6(3): 611-616.
Yamasaki, et al., "Purification and Characterization of Recombinant Human Granulocyte Colony-Stimulating Factor (rhG-CSF) Derivatives: KW-2228 and Other Derivatives" *Biosci. Biotechnol. Biochem.* (1998) 62(8): 1528-1534.
Young, et al., "Characterization of the receptor binding determinants of granulocyte colony stimulating factor" *Protein Science* (1997) 6: 1228-1236.
*Biopharmaceutical Drug Design and Development*, Edited by Susanna Wu-Pong and Yongyut Rojansakul, Humana Press (1999), Totowa, NJ: 275, 303-307.
*Biopharmaceuticals, and Industrial Perspective*, Edited by Gary Walsh and Brendan Murphy, Kluwer Academic Publishers (1999), Dordrecht, The Netherlands.
*Handbook of Process Chromatography: A Guide to Optimization, Scale-up and Validation*, Edited by Gail Sofer and Hagel Lars, (1997) Academic Press, San Diego, CA: 49-50, 65, 92-93, and 96-97.
*Preparative and Production Scale Chromatography*, Edited by G. Ganetsos, Marcel Dekker, Inc., (1993) New York, NY: 578 and 591.
Protein Purification Applications $2^{nd}$ Ed., Edited by Simon Roe, (2001) Oxford University Press, Oxford, UK.
*Protein Purification Techniques $2^{nd}$ Ed.*, Edited by Simon Roe, (2001) Oxford University Press, Oxford, UK.
Römpp Lexikon Chemie, 10. Auflage, Stchwort "Cross-flow-Filtration" (1999).
Wikipedia article on: *Cross-flow filtration*, obtained from http://en.wikipedia.org/wiki/Cross-flow_filtration, on Nov. 17, 2009.
Amersham Pharmacia Biotech, "Protein Purification Handbook", published in 2001, pp. 7, 43-51.
*Characterizing Recombinant Proteins*, obtained from http://www.nature.com/nbt/journal/v9/n10/abs/nbt1091-921.html, on Nov. 9, 2009.

\* cited by examiner

METHOD FOR THE PURIFICATION OF G-CSF

This application is the U.S. National Phase under 35 U.S.C. §371 of International Application PCT/EP2006/064263, filed Jul. 14, 2006, which claims priority to German Patent Application No. 10 2005 033 250.1, filed Jul. 15, 2005. The International Application was not published under PCT Article 21(2) in English.

The present invention relates to a method for producing recombinant granulocyte colony-stimulating factor (G-CSF), comprising at least one cation exchange chromatography and at least one hydrophobic interaction chromatography, wherein said two types of chromatographies immediately follow each other in arbitrary order. In particular, the present invention relates to a method for purifying G-CSF from a mixture of G-CSF and other proteins, comprising two cation exchange chromatography steps which are performed before and after a hydrophobic interaction chromatography, respectively.

G-CSF (granulocyte-colony stimulating factor) is a naturally occurring growth factor belonging in a broader sense to the family of cytokines and herein to the group of colony stimulating factors. G-CSF plays a decisive role in hematopoiesis and enhances the proliferation and differentiation of hematopoietic precursor cells and the activation of neutrophiles. Due to said characteristics, G-CSF has come to be used in different medical fields, like for example in the reconstitution of normal blood cell populations subsequent to chemotherapy or irradiation or for stimulating the immune response to infectious pathogens. Thus, clinically speaking, G-CSF is mainly employed in anti-tumor therapy and in particular in the treatment of neutropenia as a consequence of chemotherapy and is furthermore used in bone marrow transplantations and in the treatment of infectious diseases.

Human G-CSF in its naturally occurring form is a glycoprotein having a molecular weight of about 20,000 Dalton and five cysteine residues. Four of these residues form two intramolecular disulfide bridges which are of essential importance for the activity of the protein. As G-CSF is available only in small amounts from its natural sources, recombinant forms of G-CSF are mainly used for producing pharmaceuticals, which can for example be obtained by means of expression in mammalian cells like CHO (Chinese Hamster Ovary) cells or in prokaryotic cells like $E.$ $coli$. The recombinant proteins expressed in mammalian cells differ from naturally occurring G-CSF in that they have a different glycosylation pattern, while in the proteins expressed in $E.$ $coli$ which can have an additional N-terminal methionine residue as a result of bacterial expression, glycosylation is not present at all.

The recombinant production of G-CSF has been described in patent literature for the first time in 1987, in WO 87/01132 A1. The first commercially available G-CSF preparation on the basis of recombinant G-CSF was admitted in Germany in 1991 and is produced and distributed by Amgen under the trade name NEUPOGEN®. The recombinant production of G-CSF has been described in patent literature for the first time in 1987, in WO 87/01132 A1. The first commercially available G-CSF preparation on the basis of recombinant G-CSF was admitted in Germany in 1991 and is produced and distributed by Amgen under the trade name NEUPOGEN®.

While the production of G-CSF in prokaryotic cells is preferred as compared to the production in mammalian cells, as the use of simpler expression systems and culture conditions is possible, a frequently occurring problem in the production of recombinant proteins in prokaryotic cells is, however, the formation of hardly soluble intracellular aggregates of denatured forms of the protein expressed, the so-called inclusion bodies, which partially have a secondary structure and can be found in the cytoplasm of the bacterial cells.

The formation of said inclusion bodies leads to the necessity of solubilizing and renaturing the proteins subsequent to the isolation of the inclusion bodies by means of centrifugation at moderate speed with the aid of suitable means in order to maintain their active configuration. Herein, the competitive reaction between a transfer of the denatured protein into the right folding intermediate and an aggregation of several protein molecules is an essential factor limiting the yield of renatured protein.

In the art, several patent documents deal with the aspect of solubilizing and renaturing the proteins obtained form inclusion bodies. In EP-A-0 719 860, for example, the isolation and purification of G-CSF including solubilization and refolding are described. General techniques relating to solubilization and renaturing of denatured proteins have been described in EP-A-0 512 097, EP-A-0 364 926, EP-A-0 219 874 and WO 01/87925 and can furthermore be taken from scientific literature and standard works on protein chemistry.

Subsequently, the refolded protein is purified by means of chromatographic methods, i.e. it is separated from other proteins and further impurities which are present after solubilizing and renaturing.

WO 87/01132 A1 already mentioned in the above, wherein the production of G-CSF in $E.$ $coli$ host cells has been described for the first time, also deals with chromatographic purification. Within the scope of the purification of the recombinant G-CSF, a cation exchange chromatography using a CM cellulose column is described in Example 7 of WO 87/01132 A1.

In EP 0 719 860 A1, the G-CSF is purified subsequently to solubilization and oxidation by means of Dowex in order to remove the solubilizing agent, followed by an anion exchange chromatography and a cation exchange chromatography. In EP 0 719 860 A1, CM sepharose is also used for the cation exchange chromatography.

In WO 03/051922 A1, a purification method for G-CSF is described, wherein a metal affinity chromatography is performed; more exactly, a chromatography on immobilized metal (immobilized metal affinity chromatography, IMAC). Subsequently to the metal affinity chromatography, a cation exchange chromatography and/or a gel filtration may be performed according to WO 03/051922.

In WO 01/04154 A1, a method for purifying G-CSF is described, wherein first a hydrophobic interaction chromatography and a subsequent hydroxyapatite chromatography are conducted. Subsequently to the hydroxyapatite chromatography, a cation exchange chromatography is performed.

It is a problem underlying the present invention to disclose a method for purifying biologically active recombinant human G-CSF, by means of which it is possible to obtain G-CSF with satisfactory purity and yield. Herein, the method should be as simple and straightforward in conduction as possible. Desirable is a purification method that can be conducted with as few chromatographic steps as possible in order to keep technical complexity and costs on a low level and to avoid high losses of protein.

This and further problems are solved by means of the method given in claim 1. Preferred embodiments are described in the dependent patent claims.

It has been found that it is possible in the chromatographic purification of renatured G-CSF by means of a cation exchange chromatography and a hydrophobic interaction chromatography to achieve acceptable purity of the recombinant biologically active G-CSF with a satisfactory yield. Purity can be further increased by means of a second cation exchange chromatography step.

Thus, the present invention relates to a method for purifying recombinantly produced biologically active human G-CSF in which at least one cation exchange chromatography and at least one hydrophobic interaction chromatography are conducted, wherein said chromatographic steps are performed in arbitrary order, provided that there is not performed any other chromatographic step or any other purification step between said steps. Thus, cation exchange chromatography and hydrophobic interaction chromatography are immediately consecutive.

According to the present invention, the term "biologically active human G-CSF" is understood to denote that G-CSF which has been purified by means of the method according to the present invention is capable of enhancing the differentiation and proliferation of hematopoietic precursor cells and of causing the activation of mature cells of the hematopoietic system. Thus, the G-CSF obtained by means of the method according to the present invention is suitable for treating indications in case of which the administration of G-CSF is advantageous. It is understood, that the term "biologically active human G-CSF" also includes mutants and modifications of G-CSF, whose amino acid sequence is altered as compared to the wild type sequence, but which have a similar biological activity as the wild type G-CSF like those, for example, that are described in WO 01/87925 and EP 0 456 200. The same applies to G-CSF conjugates. Preferably, the G-CSF to be purified is human Met-G-CSF produced in *E. coli* cells.

In one embodiment of the present invention, the method for purifying G-CSF comprises two cation exchange chromatography steps which are conducted before and after the hydrophobic interaction chromatography, respectively.

In a further embodiment of the present invention, the method comprises a tangential flow filtration subsequent to the only or—in case more than one cation exchange chromatography steps are conducted—the last cation exchange chromatography.

In a further embodiment, conducting an anion exchange chromatography is omitted in the method for purifying G-CSF.

In a further embodiment, the purification method according to the present invention is sufficient without gel filtration chromatography.

In a further embodiment of the present invention, conducting a preparative HPLC is omitted. The same applies to reversed phase chromatography, which is to be distinguished from the hydrophobic interaction chromatography according to the present invention and which is possibly also omitted in the preparation. rpHPLC is only employed for analytical purposes.

In a further embodiment, no affinity chromatography, in particular no dye, metal or immunoglobulin affinity chromatography, is conducted within the scope of the method.

In a further embodiment, conducting a hydroxyapatite chromatography is omitted within the scope of the purification method.

Thus, in a preferred embodiment, the purification method according to the present invention utilizes only two different chromatographic separation methods, namely the method of ion exchange on the basis of competitive interaction of charged ions and the method of hydrophobic interaction, which is characterized in that the nonpolar surface regions of a protein adsorb to the weakly hydrophobic ligands of a stationary phase at high salt concentrations.

To be distinguished therefrom is the chromatographic separation principle of affinity which is based on the specific and reversible adsorption of a molecule to an individual matrix-bound bonding partner. The hydroxyapatite chromatography, which is based on the use of inorganic hydroxyapatite crystals, is a further separation method which differs from the ion exchange chromatography in form of cation exchange chromatography and hydrophobic interaction chromatography.

Said chromatographic principles mentioned are also correspondingly distinguished among experts (see, for example, Bioanalytik, F. Lottspeich, H. Zorbas (ed.), Heidelberg, Berlin, Germany, Spektrum Akad. Verlag 1998).

In a preferred embodiment, the chromatographic purification does not comprise more than three chromatographic steps, in which only two different chromatographic separation methods are employed.

Renatured G-CSF, which is supposed to be transferred to achieve a purity that allows its use in the form of a pharmaceutical preparation, is employed as starting material for chromatographic purification.

Herein, solubilizing and refolding the protein can be conducted according to the methods known in the art, for example as described in EP-A-1 630 173.

The refolded G-CSF can be prepared subsequent to refolding and previous to the first chromatographic step, for example by means of filtration, concentration, precipitation, acidification and/or dialysis.

In many cases it will be advantageous to purify the folding setup previous to the first chromatographic step, i.e. to remove high-molecular particles, which are mostly protein aggregates that have been formed in folding. Said purification can be conducted by means of depth filtration, wherein a granulate bulk material serves as filter means. The solid particles are larger than the pores of the filter means or are held back by absorption at the inner surface of the bulk.

In depth filtration, the use of cellulose ester fibers as filter means is preferred. Suitable filter means as well as corresponding instructions for use are, for example, available from Millipore under the trade names Millistak Plus C0HC and Millistak+B1HC.

Preferably, the folding setup is acidified previous to the depth filtration, so that the filtrate can be immediately employed for the cation exchange chromatography in a particularly efficient manner. Herein, the ph value of the folding setup is preferably set to below 4.0, particularly preferably to 3.2.

For the cation exchange chromatography, conventional commercially available matrices can be employed. Herein, the G-CSF binds to the cation exchange matrix within a specific pH range due to its positive total charge, while most of the contaminating substances like nucleic acids, lipopolysaccharides and proteins originating from host cells as well as ionic isomers of G-CSF and altered forms of G-CSF having different pH values are not capable of binding or of being removed by means of washing.

Suitable cation exchange matrices include, but are not limited to, carboxymethyl (CM) cellulose, AG 50 W, Bio-Rex 70, carboxymethyl (CM) Sephadex, sulfopropyl (SP) Sephadex, carboxymethyl (CM) sepharose CL-6B, CM sepharose HP, Hyper D-S ceramic (Biosepra) and sulfonate (S) sepharose, SP sepharose FF, SP sepharose HP, SP sepharose XL, CM sepharose FF, TSK gel SP 5PW, TSK gel SP-5PW- HR, Toyopearl SP-650M, Toyopearl SP-650S, Toyopearl SP-650C, Toyopearl CM-650M, Toyopearl CM-650S, Macro-Prep High S Support, Macro-Prep S Support, Macro-Prep CM Support etc.

Suitable matrices and protocols for conducting the cation exchange chromatography can be taken from the product information of suppliers like Amersham Biosciences (http://www.amershambiosciences.com, now GE Healthcare) or Bio-Rad (http://www.bio-rad.com) by the person skilled in the art.

Sulfopropyl matrices, in particular the products SP Sepharose XL and SP Sepharose FF (Fast Flow), available by Amersham Biosciences, Freiburg, Germany (now GE Healthcare), are preferably used as matrix for the cation exchange chromatography.

In a preferred embodiment of the present invention, in which two cation exchange chromatographies are conducted, namely before and after the hydrophobic interaction chromatography, respectively, a sulfopropyl matrix is employed in both cases, particularly preferably SP Sepharose XL in the first cation exchange chromatography and SP Sepharose FF in the second cation exchange chromatography.

Suitable buffers for the cation exchange chromatography include maleate, malonate, citrate, lactate, acetate, phosphate, HEPES and Bicin buffers. Preferably, the concentration of the buffer lies between 10 and 100 mM, preferably between 20 mM and 50 mM. For purifying the G-CSF, the pH value of the buffer should possibly not be higher than 7.0, preferably not higher than 6.5.

In a preferred embodiment, 20 mM sodium acetate, pH 5.0, which is employed for equilibrating and washing, is used for the cation exchange chromatography.

In case a second cation exchange chromatography is conducted, 50 mM sodium phosphate, pH 5.4, is herein preferably used for equilibrating and washing.

Subsequently to washing, the G-CSF can be eluted from the column by means of an alteration, in case of the cation exchange chromatography by means of an increase in pH value or an increase in ionic strength.

Preferably, the elution is effected by means of increasing the ionic strength. In case 20 mM sodium acetate, pH 5.0, is used as buffer, a solution of 20 mM sodium acetate, pH 5.0, and 200 mM NaCl is, for example, suitable for the elution.

Further suitable conditions for the cation exchange chromatography can be taken from the relevant literature, like for example from the manual "Ion Exchange Chromatography—Principles and Methods" by Amersham Biosciences, Freiburg, Germany (now GE Healthcare), 2002.

The salt concentration in the charging buffer for the cation exchange chromatography should be sufficiently low in order to allow binding to the matrix, wherein binding also depends on the pH value of the solution.

Within the scope of the cation exchange chromatography, different buffers can be employed for charging and binding to the matrix, for example buffers selected from the group consisting of acetate, citrate, Tris/HCl, Tris/acetate, phosphate, succinate, malonate, 2-(N-morpholinoethanesulfonate) (MES) and other buffers.

After charging the column, the column is washed and subsequently the proteins are eluted from the column. Herein, the elution can be conducted by means of increasing the ionic strength, which is effected by means of increasing the salt concentration in the buffer solution. Alternatively, an increase in pH value is suitable. Herein, discontinuous step gradients, linear gradients or a suitable combination of such gradients can be employed.

Elution buffers suitable for washing and for the elution can be selected from acetate, citrate, Tris/HCl, Tris/acetate, phosphate, succinate, malonate, MES and other suitable buffers with the addition of salts like NaCl or KCl. The ionic strength and the salt concentration, by means of which the elution is achieved, are dependent on the pH value of the buffer solution. The higher the pH value of the buffer, the lower is the ionic strength that is required for the elution of the proteins from the column.

The hydrophobic interaction chromatography can also be conducted with conventional matrices. Suitable are matrices like butyl, phenyl or octyl sepharose (Amersham Biosciences, now GE Healthcare), Makro-Prep-methyl or t-butyl (Bio-Rad) and Fractogel EMD with propyl or phenyl ligands (Merck).

Preferably, the hydrophobic ligands are butyl, phenyl or octyl groups, particularly preferably they are phenyl groups. Herein, the products by Amersham Biosciences (now GE Healthcare) can be employed.

Suitable matrices and protocols for conducting the cation exchange chromatography can be taken from the product information of suppliers like Amersham Biosciences, now GE Healthcare) or Bio-Rad by the person skilled in the art.

Preferably, the matrix is Phenyl Sepharose HP (High Performance), available by Amersham Biosciences (now GE Healthcare).

Conventional buffers, which are also employed in other types of chromatography, are suitable as buffers for the hydrophobic interaction chromatography. In a preferred embodiment, a citrate buffer is used. Advantageously, the elution is conducted by means of increasing the pH value. A pH gradient from about pH 3.0 to about 6.0 has proven to be particularly suitable.

Further conditions suitable for the hydrophobic interaction chromatography can be taken from the relevant literature, like for example from the manual "Hydrophobic Interaction Chromatography—Principles and Methods" by Amersham Biosciences (now GE Healthcare), Freiburg, Germany, 2002.

In general, the person skilled in the art is familiar with the chromatographic principles utilized in the method according to the present invention; in any case, they are described in detail in established manuals or protocols by the suppliers of chromatography matrices, columns and other means.

The tangential flow filtration (TFF), which is conducted within the scope of one embodiment of the present invention subsequently to the chromatic purification, in particular subsequently to the only or the last cation exchange chromatography, can be conducted by means of conventional TFF systems and protocols, like for example supplied by the companies Millipore and Pall Corporation. The TFF is a filtration as an additional purification step in contrast to the previous purification steps of the cation exchange chromatography and the hydrophobic interaction chromatography.

The G-CSF purified within the scope of the present invention is expressed in host cells by means of conventional gene-technological methods. Preferably, it is human G-CSF. Various expression systems for the expression in *E. coli* cells are commercially available. Suitable is, for example, the expression of human G-CSF under the control of an inducible promoter, for example an IPTG-inducible promoter, see for example Sambrook and Russel, Molecular Cloning—A Laboratory Manual, $3^{rd}$ edition 2001, Cold Spring Harbor Laboratory Press, Cold Spring Harbor, N.Y., USA, chapter 15, or established manufacturers' protocols, for example by Proinega or Stratagene.

Fermentation is conducted according to standard protocols, like they are described in patent and scientific literature, for example in a two-step process consisting of a batch cultivation and a fed batch cultivation.

Harvesting the so-called inclusion bodies containing the G-CSF overexpressed in E. coli and the lysis of said inclusion bodies have partly been described in the patent literature discussed in the above. However, suitable protocols can also be found in standard works on protein chemistry as well as in laboratory manuals. The same applies for solubilizing and refolding, which are objects of various patent documents, as has been discussed in the above.

The invention also relates to pharmaceutical preparations containing the G-CSF obtained according to the present invention. The G-CSF obtained can either be stored in the form of a lyophilisate or in liquid form. It is administered either subcutaneously or intravenously. Suitable adjuvants in the formulations of the recombinantly expressed G-CSF are, for example, stabilizers like sugar and sugar alcohols, amino acids and tensides like for example polysorbate 20/80 as well as suitable buffer substances. Examples for formulations are described in EP 0 674 525, EP 0 373 679 and EP 0 306 824, see also the trade products NEUPOGEN® and Granocyte in the "ROTE LISTE 2004".

EXAMPLES

The following examples are intended to illustrate the present invention without limiting the scope thereof.

The human G-CSF was expressed under the control of an IPTG-inducible promoter in E. coli cells. Examples for suitable expression systems can be taken, for example, from the laboratory manual Sambrook and Russell, Molecular Cloning—A Laboratory Manual, $3^{rd}$ edition, 2001, Cold Spring Harbor Laboratory Press, Cold Spring Harbor, N.Y., USA, chapter 15, or from established manufacturers' protocols, for example by Promega or Stratagene.

The fermentation was conducted according to standard protocols, like they are described in patent and scientific literature, in a two-step process comprising a batch cultivation and a fed batch cultivation. The bacteria were cultivated for 17 to 18 hours before they were stimulated by means of adding 1 mM IPTG to form the recombinant G-CSF. The induction period was 4.0 hours.

Harvesting the bacteria was conducted by means of beaker centrifugation for 20 min at 5,000 g and 4° C. After the centrifugation, the supernatant was discarded and the cells were filled up again with buffer (20 mM sodium phosphate, pH 7.0; 1 mM EDTA) to the fermentation volume before they were lysed by means of three passages at 800 bar. Subsequently, the lysate was purified by means of separation (CSA1-Separator, Westfalia, Oelde, Germany).

Concentrating the Inclusion Bodies

In principle, the suspension of the inclusion bodies that has been obtained by harvesting can immediately be used for the subsequent solubilization. In this case, however, the maximum achievable protein concentration in the solubilisate is strongly limited, which may lead to limitations during folding. Thus, the suspension of the inclusion bodies should be concentrated by means of centrifugation subsequently to harvesting and washing in order to achieve a high protein concentration in the solubilisate.

The suspension of the inclusion bodies was centrifuged for 20 minutes at 10,000 g in a beaker centrifuge. The paste of inclusion bodies that is obtained by means of centrifugation can be stored at −20° C. for at least 12 weeks.

Solubilization

In order to allow effective solubilization of larger pellets of inclusion bodies in a relatively short time, mechanical crushing of said pellets, for example by means of Ultra Turrax treatment, is furthermore required. The paste of the inclusion bodies that was obtained by means of centrifugation was weighed, mixed with 9.0 ml solubilizing buffer (30 mM Tris, 1 mM EDTA, 6.0 M guanidine-HCl, 100 mM GSH, pH 8.0) per gram inclusion bodies and crushed by means of Ultra Turrax treatment. The setup was thoroughly vortexed and was then incubated on a roller mixer or a magnetic stirrer at room temperature for about 2 hours.

Refolding

The protein concentration in the solubilisate was determined by means of the method according to Bradford using BSA as standard protein. For folding, the amount necessary to achieve a protein concentration of 700 µg/ml in a desired amount of buffer was added to the refolding buffer (30 mM Tris, 2 mM GSSG, 2 mM GSH, 3 M urea, pH 7.5; 4° C.). The corresponding amount of solubilisate was added slowly and steadily while stirring with a magnetic stirrer in order to avoid locally increased concentrations of solubilisate or protein. The afflux speed and the mode of mixing can be adjusted to the respectively employed volume of solubilizing setup. After the addition of the solubilisate had been completed, the setup was incubated for at least 12 hours at 4° C. During this period no further mixing was required.

Depth Filtration

Subsequently to refolding, the refolding setup is filtrated before the first chromatographic step is conducted. Herein, for example, a depth filter can be used for the filtration, for example a suitable filter by Millipore, Schwalbach, Germany. Previously to the filtration, the pH value is adjusted to pH 3.2 by means of 2 M citric acid.

Conducting the First Cation Exchange Chromatography

The first chromatographic step serves for capturing the target protein and separates refolding agents like urea, GSH, GSSG, as far as those are present in the folding setup, from the target protein. In said step, incorrectly folded protein species and host cell proteins are also separated. Here, a cation exchange chromatography is employed. SP Sepharose XL by Amersham Biosciences (now GE Healthcare) is used as matrix. The chromatography is conducted at pH 5.0.

The SP Sepharose XL matrix was equilibrated with 1.5 column volumes of 20 mM sodium acetate, pH 5.0. The filtered refolding setup was loaded onto the column and was subsequently washed with 1.5 column volumes washing buffer (20 mM sodium acetate, pH 5.0). Subsequently, the G-CSF was eluted from the column with 3 column volumes elution buffer (20 mM sodium acetate, 200 mM NaCl, pH 5.0). The purity of the eluted G-CSF was determined by means of rpHPLC; it was higher than 80%. As related to the filtered folding setup, the yield was also higher than 80%.

Conducting the Hydrophobic Interaction Chromatography

In the second chromatographic step, a further purification of the G-CSF is conducted on the basis of the eluate of the SP Sepharose XL. In particular the product-related contaminations are substantially depleted. Here, a hydrophobic interaction chromatography with Phenyl Sepharose HP by Amersham Biosciences (now GE Healthcare) is conducted.

The Phenyl Sepharose HP column was first equilibrated with 2 column volumes of 12% buffer B, 88% buffer A (buffer B: 20 mM sodium citrate, pH 6.7; buffer A: 20 mM sodium citrate, pH 2.7, 110 mM NaCl). Then, the eluate of the SP Sepharose XL column, which had previously been diluted with 5 volumes of buffer A (20 mM sodium citrate, pH 2.7, 110 mM NaCl), was applied onto the column.

Subsequently, the column was washed with 2 column volumes of 12% buffer 13, 88% buffer A and a linear gradient from 12% to 90% buffer B was run in 5-8 column volumes. The elution occurred within the scope of said linear pH gradient from about pH 3.0 to about 6.0. Finally, the column was rinsed with 3 column volumes of 90% buffer B, 10% buffer A.

The elution fractions were tested for their purity by means of rpHPLC and fractions having a purity higher than 95% were combined.

The G-CSF obtained after the hydrophobic interaction chromatography had a purity of more than 96%. The yield from the HIC step was almost 80%.

Conducting the Second Cation Exchange Chromatography

In the third chromatographic step, a further purification of the G-CSF to a purity of more than 99% is conducted on the basis of the eluate of the Phenyl Sepharose HP. In particular the product-related contaminations are substantially depleted. Here, a cation exchange chromatography is again employed. The SP Sepharose FF by Amersham Biosciences (now GE Healthcare) is used herein.

The SP Sepharose FF column was equilibrated with 3 column volumes of 100% buffer A (50 mM sodium phosphate, pH 5.4). Subsequently, the eluate of the hydrophobic interaction chromatography was applied onto the column and the column was rinsed with 2 column volumes of 100% buffer A (50 mM sodium phosphate, pH 5.4). Herein, the sample that was applied contained about 60 mM NaCl and had a pH value of 4.0-4.2. The elution was conducted by means of a combination of step and linear pH gradient. The first step ran up to 10% buffer B (50 mM sodium phosphate, pH 6.4) and maintained said concentration for 1.5 column volumes. This was followed by a gradient over 1 column volume from 10 to 15% buffer B (50 mM sodium phosphate, pH 6.4). G-CSF was eluted in a linear gradient from 15% to 35% buffer B (50 mM sodium phosphate, pH 6.4) over 12.5 column volumes, wherein collecting the eluate with increasing absorption was conducted at 280 mm. Finally, the column was rinsed in one step to 100% buffer B (50 mM sodium phosphate, pH 6.4).

The elution fractions were tested for their purity by means of rpHPLC and fractions having a purity of more than 99% were combined. The total yield was 80%.

The Met-G-CSF that was obtained as a result of the chromatographic steps described in the above had a purity of at least 99.5% after all HPLC analyses (rp, SEC and IEX).

Determining the contaminations also resulted in a very strong depletion of DNA, endotoxin and host cell protein.

Determining the Biological Activity

The activity of the G-CSF obtained by the method according to the present invention was determined by means of a bioassay and was compared to the activity of a standard, commercially available G-CSF (NEUPOGEN® To this end, the mouse cell line NFS-60 was used, which is responsive to G-CSF. Said cell line was cultivated in RPMI 1640 medium (Bachem, Heidelberg, Germany), which contained 1.5 g/l sodium carbonate, 4.5 g/l glucose, 10 mM Hepes and 1.0 mM sodium pyruvate and had been supplemented with 2 mM glutamine, 10% FCS, 0.05 mM 2-mercaptoethanol and 60 ng/ml G-CSF.

For the activity test, the cells were washed twice with medium without G-CSF, placed in 96-well plates at a concentration of $2\times10^4$ cells per well and were incubated for three days at 37° C. and 4.5% $CO_2$ with varying concentrations of the purified G-CSF and the standard. Subsequently, the cells were stained with XTT reagent and the absorption at 450 nm was measured in a microtiter plate reader. It showed that the cells that had been treated with the G-CSF purified according to the present invention grew just as well as those cells that had been treated with the standard, which led to the conclusion that both G-CSF samples had the same biological activity.

In the gel electrophoretic analyses (SDS-PAGE, Western Blot, isoelectric focusing), the Met-G-CSF obtained after the chromatographic purification also behaved like the NEUPOGEN® used as standard.

In order to determine the folding yield, an rpHPLC, wherein the protein is denatured, may be conducted subsequently to obtaining the G-CSF. Due to maintained disulfide bridges, different disulfide-bridged species often have different hydrophobic surfaces and can therewith be separated in the rpHPLC. Thus, only the detection of the correct disulfide bridge can be conducted with said method. The former, however, is a decisive and for many small and correspondingly bridged proteins an already sufficient criterion for correct folding. A size exclusion (SE)-HPLC can also be conducted as a further analysis method.

Suitable materials and protocols for conducting the rpHPLC or the SE-HPLC can be taken from the product information by suppliers like Vydac or TOSOH Bioscience by the person skilled in the art. Determining the yield of Met-G-CSF is also described in Herman et al, (1996) Pharm. Biotechnol. 9: 303-328). Herein, the exact proportion of Met-G-CSF is determined by means of integration of the peak area and conversion on the basis of the extinction coefficient.

Subsequently to purification, the G-CSF can be analyzed with respect to its amount and its activity. A qualitative analysis can be conducted via an SDS-PAGE analysis with subsequent Coomassie Brilliant Blue Staining or an rpHPLC. A commercially available G-CSF preparation can be used as standard for the analyses. In addition, a peptide map or a mass spectroscopy can be conducted. The activity of the G-CSF purified can be determined by means of different biological test methods, like they are, for example, described in Shirafuji et al. (1989) Exp. Hematol. 17 (2): 116-119; Oh-Eda et al. (1990) J. Biol. Chem. 265 (20): 11432-11435; Stute et al. (1992) Blood 79 (11): 2849-2854 and Oshima et al. (2000) Biochem. Biophys. Res. Commun. 267 (3): 924-927.

Incidentally, all chromatographies are conducted according to the recommendations and protocols of the suppliers of the matrices or the columns (for example with respect to flow rate, column volumes employed for washing or for elution, diameters and bed heights of the columns, etc.).

The invention claimed is:

1. A method of purifying granulocyte-colony stimulating factor (G-CSF), said method comprising:
   (a) subjecting a refolded G-CSF composition to cation exchange chromatography to achieve a purity of at least about 80%;
   (b) subjecting the cation-exchange-chromatography-purified G-CSF composition of step (a) to hydrophobic interaction chromatography to achieve a purity of at least about 96%;
   (c) subjecting the hydrophobic-interaction-chromatography-purified G-CSF composition of step (b) to cation exchange chromatography to achieve a purity of at least about 99%; and
   (d) subjecting the cation-exchange-chromatography-purified G-CSF composition of step (c) to a tangential flow filtration step;
   wherein said G-CSF was expressed in *E. coli* before being refolded; and wherein no affinity chromatographic steps are included in the purification method.

2. The method of claim 1, wherein said cation-exchange-chromatography step (a) comprises eluting G-CSF from a cation-exchange-chromatography column using a buffer having a NaCl concentration of at least 200 mM NaCl.

3. The method of claim 1, wherein said hydrophobic-interaction-chromatography step (b) comprises Phenyl Sepharose HP as a chromatography matrix.

4. The method of claim 2, wherein said hydrophobic-interaction-chromatography step (b) comprises using Phenyl Sepharose HP as a chromatography matrix.

5. The method of claim 1, wherein the cation exchange matrix used in said cation-exchange-chromatography step (a) comprises carboxymethyl groups.

6. The method of claim 1, wherein the cation exchange matrix used in said cation-exchange-chromatography step (a) comprises sulfopropvl groups.

7. The method of claim 1, wherein the same type of cation exchange matrix is used for the cation exchange chromatography steps in step (a) and step (c).

8. The method of claim 7, wherein the cation exchange matrix comprises sulfopropyl groups.

9. The method of claim 1, wherein the hydrophobic interaction matrix comprises hydrophobic ligands selected from butyl, phenyl, and octyl groups.

10. The method of claim 9, wherein the hydrophobic interaction matrix comprises phenyl hydrophobic ligands.

11. A method of purifying granulocyte-colony stimulating factor (G-CSF) said method comprising:
  (a) subjecting a refolded G-CSF composition to cation exchange chromatography using a matrix comprising sulfopropyl groups to achieve a purity of at least about 80%;
  (b) subjecting the cation-exchange-chromatography-purified G-CSF composition of step (a) to hydrophobic interaction chromatography using a matrix comprising a hydrophobic ligand comprising phenyl groups to achieve a purity of at least about 96%;
  (c) subjecting the hydrophobic-interaction-chromatography-purified G-CSF composition of step (b) to cation exchange chromatography using a matrix comprising sulfopropyl groups to achieve a purity of at least about 99%; and
  (d) subjecting the cation-exchange-chromatography-purified G-CSF composition of step (c) to a tangential flow filtration step;
wherein said G-CSF was expressed in E. coli before being refolded; and
wherein no affinity chromatographic steps are included in the purification method.

12. A method of purifying granulocyte-colony stimulating factor (G-CSF), said method comprising:
  (a) subjecting a refolded G-CSF composition to cation exchange chromatography using a matrix comprising sulfopropyl or carboxylmethyl groups to achieve a purity of at least about 80%;
  (b) subjecting the cation-exchange-chromatography-purified G-CSF composition of step (a) to hydrophobic interaction chromatography using a matrix comprising hydrophobic ligands selected from butyl, phenyl or octyl groups to achieve a purity of at least about 96%;
  (c) subjecting the hydrophobic-interaction-chromatography-purified G-CSF composition of step (b) to cation exchange chromatography using a matrix comprising sulfopropyl or carboxymethyl groups to achieve a purity of at least about 99%; and
  (d) subjecting the cation-exchange-chromatography-purified G-CSF composition of step (c) to a tangential flow filtration step;
wherein said G-CSF was expressed in E. coli before being refolded; and
wherein no affinity chromatographic steps are included in the purification method.

13. The method of claim 12, wherein in step (a), the cation exchange chromatography matrix comprises carboxylmethyl groups.

14. The method of claim 12, wherein in step (a), the cation exchange chromatography matrix comprises sulfopropyl groups.

15. The method of claim 12, wherein in step (b), the hydrophobic ligands are phenyl groups.

* * * * *